US00PP14213P29

(12) United States Plant Patent
Whiddon

(10) Patent No.: US PP14,213 P2
(45) Date of Patent: Oct. 7, 2003

(54) *CAMELLIA SASANQUA* PLANT NAMED 'TDN 1116'

(50) Latin Name: *Camellia sasanqua*
Varietal Denomination: TDN 1116

(75) Inventor: Donald Paul Whiddon, Semmes, AL (US)

(73) Assignee: Plant Development Services Inc., Coxley, AL (US)

( * ) Notice: Subject to any disclaimer, the term of this patent is extended or adjusted under 35 U.S.C. 154(b) by 0 days.

(21) Appl. No.: 09/259,049

(22) Filed: Mar. 1, 1999

(51) Int. Cl.[7] ..... A01H 5/00
(52) U.S. Cl. ..... Plt./245
(58) Field of Search ..... Plt./245

(56) References Cited

U.S. PATENT DOCUMENTS

PP1,107 P * 6/1952 Hastie, Jr. ..... Plt./245

OTHER PUBLICATIONS

Encore Plants Expect more brochure, insert for 'Hot Flash' Dec. 10, 1999.*

* cited by examiner

*Primary Examiner*—Bruce R. Campell
*Assistant Examiner*—W C Haas

(57) ABSTRACT

A new and distinct variety of *Camellia sasanqua* found in an openly pollinated group of seedlings. The new variety is unique with its dense, low, and spreading growth habit, improved growth rate, and strong red semi-double flowers.

1 Drawing Sheet

CROSS REFERENCE TO RELATED APPLICATIONS

This application is related to Ser. Nos. 09/259,047; 09/259,050 and 09/259,048, all now abandoned.

Botanical designation: *Camellia sasanqua.*

BACKGROUND OF THE INVENTION

This new Camellia variety was discovered by Donald Paul Whiddon in a group of *Camellia sasanqua* seedlings of unknown parentage growing in a cultivated area in Semmes, Ala. The seedling was found in the spring of 1990. The new and distinct *Camellia sasanqua* plant of this invention comprises a novel and valuable plant with its unique bloom color, bloom form, and growth habit.

Asexual propagation of the new plant by cuttings has been under Mr. Whiddon's direction at the same location. The new plant retains its distinctive characteristics and reproduces true to type in successive generations. The plant cannot be reproduced true from seed.

SUMMARY OF THE INVENTION

The following are the most outstanding and distinguishing characteristics of this new cultivar when grown under normal horticultural practices in Semmes, Ala.

1. Moderate growth rate under normal fertilization and moisture conditions.
2. A uniformly dense, low and spreading growth habit 5–6' tall and 5–6' wide.
3. A strong red flower color Red Group 53B.
4. Semi-double flower 2¾–3¼" in diameter.
5. Good specimen plant.
6. Desirable in planters.
7. Makes a good espalier plant.

8. Very good foundation plant.
9. Hardy to Zone 7b.
10. Attractive glossy foliage.
11. Performs well in sun or partial shade.
12. Has the ability to be sheared and trimmed to be kept within prescribed limits.
13. Makes a good low-growing sheared or natural hedge.
14. Easily propagated.

DESCRIPTION OF THE DRAWINGS

This new *Camellia sasanqua* variety is illustrated by the accompanying photographic prints in which.

1.

2.

Figure 1:
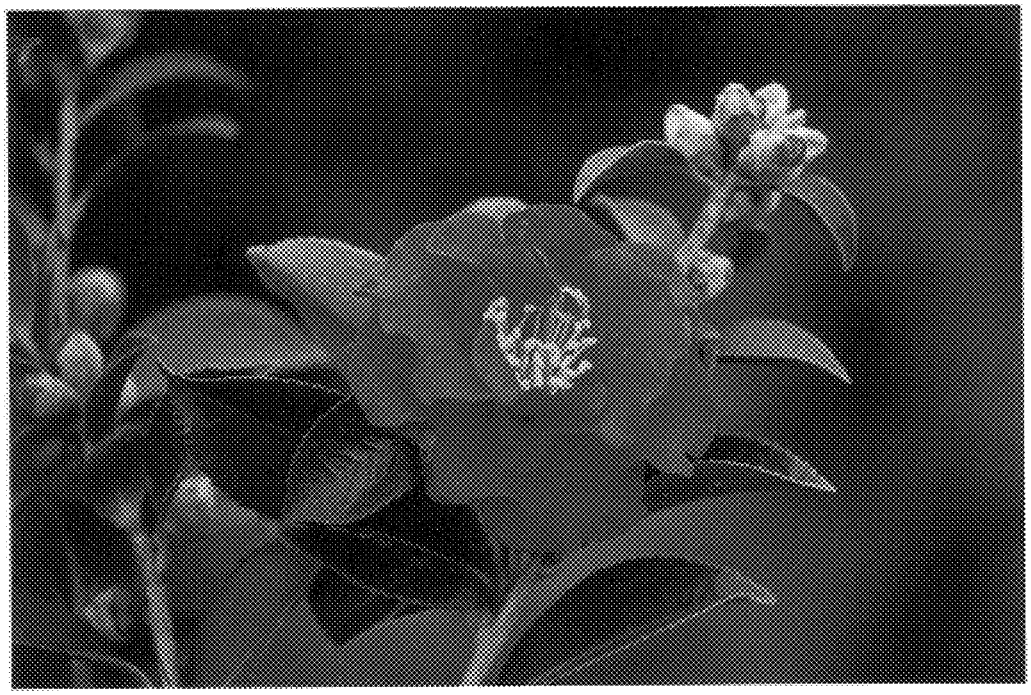
FIG. 1 is a close-up showing flower, buds, foliage, and stem color as well as flower size and form. Stipules are not present due to their caducous nature.
Figure 2:
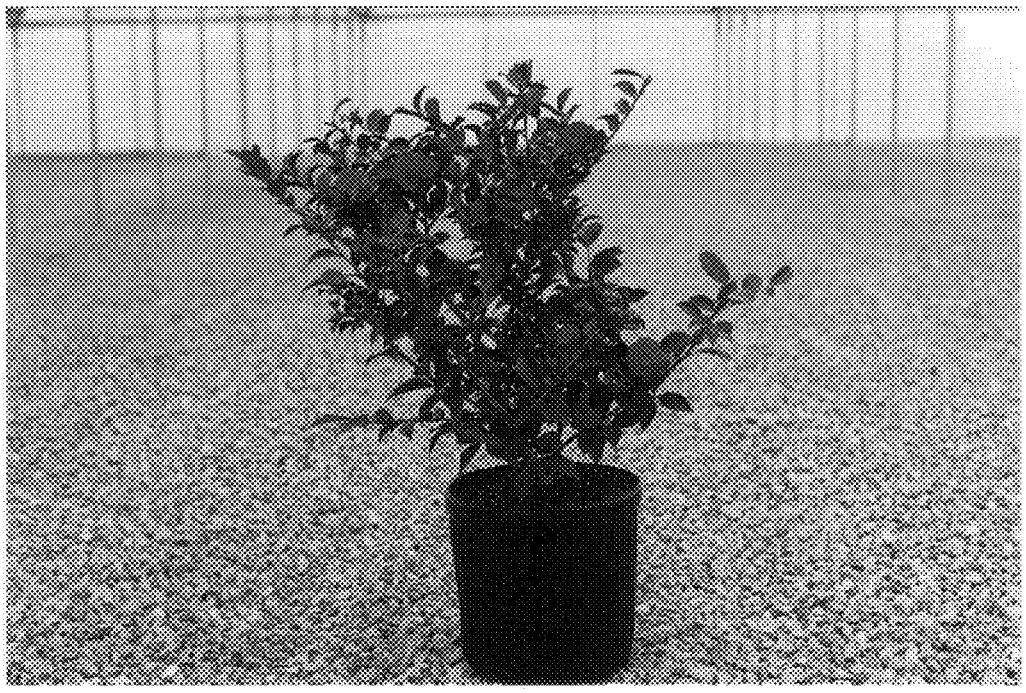
FIG. 2 shows the dense, low and spreading growth habit of a three gallon plant.

The colors shown are as true as is reasonably possible to obtain by conventional photographic procedures. Colors in the photographs may appear different than actual colors due to light reflectance. The colors of the various plant parts are defined with reference to The Royal Horticultural Society Colour Chart. Descriptions of colors in ordinary terms are presented where appropriate for clarity in meaning.

BOTANICAL DESCRIPTION OF THE PLANT

The following is a detailed description of the new variety of Camellia based on my observations made of 2 year old plants grown in 3 gallon containers in wholesale commercial production practices, in greenhouses, and in established landscape plantings in Semmes, Ala. The comparisons are in reference to the best know "usual" characteristics of the plants.

Distinctive Characteristics

| Characteristic | *C. sasanqua* 'TDN 1116' | *C. sasanqua* 'Shi Shi Gashira' | *Camellia japonica* (The Species) |
|---|---|---|---|
| Height (Mature) | 5–8' | 5–6' | 10–15' |
| Width (Mature) | 5–8' | 5–6' | 6–15' |
| Flower Size | 2¾–3¼" | 2½–3" | 3–6" |
| Bloom Period | Nov.–Dec. | Nov.–Dec. | Nov.–May |
| Flower Color | Red G 53B | Red-Purple G. 66D | White–Red (Range) |
| Leaf Length | 2–2½" | 2–2¼" | 2–4" |
| Leaf Width | 1–1¼" | 1⅛–1½" | 1–2" |
| Leaf Shape | Elliptic | Elliptic | Ovate–elliptic |
| Pubescent (immature petioles and midribs) | Yes | Yes | No |
| Growth Rate | Moderate | Slow | Moderate |

The plant from which the varieties 'TDN 1116' and 'Shi Shi Gashira' originated has the botanical name Theaceae *Camellia sasanqua*. The family name Theaceae was proposed by David Don (1799–1841). The author of the genus name Camellia is Carolus Linnaeus (1707–1778) and the species name sasanqua was first published by Carl Pehr Thunberg (1743–1828). The new variety is sold under the trade name Hot Flash and is listed as *Camellia sasanqua* Hot Flash™ 'TDN 1116'.

*Camellia sasanqua* 'Shi Shi Gashira' is an unpatented variety which is very popular in the industry. It is comparable to the new plant in that both are low growing and have similar flower colors. However, there are differences. The growth rate of 'TDN 1116' is more rapid than that of 'Shi Shi Gashira' and the flower is slightly larger and a darker red.

The species *Camellia japonica* is also similar to the new variety and is very popular in the nursery industry. The species *Camellia japonica* differs in that it has larger leaves and flowers, glabrous leaves and stems, a later bloom period, and is slightly less cold hardy.

The cultivar 'TDN 1111' (U.S. plant patent application Ser. No. 09/259,047, now abandoned) is comparable to 'TDN 1116', however, there are differences. 'TDN 1111' has an upright growth habit 12–15' tall and a strong pink flower Red-Purple Group 63A.

Classification:
Botanic: *Camellia sasanqua* 'TDN 1116'.
Form: Dense, low, and spreading.
Texture: Medium.
Height: 5–6'.
Width: 5–6'.

Growth habit: Dense, low and spreading shrub. Moderate growth rate under normal fertilization and moisture conditions.

Foliage: Alternate, simple, evergreen, elliptic, and varying in size from 2" to 2½" long and 1" to 1¼" wide. The margins are crenulate, with a petiole ⅛" to ¼" long and Yellow-Green Group 144B. Midveins and laterals are prominent on the upper leaf surface and the midvein is prominent on the underside. The base of the leaf is acute and the apex is abruptly acuminate. The upper surface of the mature leaf is closest to Yellow-Green Group 147A, glossy and glabrous. The underside is Yellow-Green Group 146A. These mature leaf colors are persistent throughout the winter. The immature leaves are pubescent on the midrib above and below. Immature petioles are also pubescent. As the leaf matures this pubescence is lost. The upper surface of the immature leaf is Greyed-Orange Group 165A and glossy. The underside is Yellow-Green Group 146C and matte. The immature midribs, top and bottom, are Yellow-Green Group 146C and mature to Yellow-Green Group 144B. The alternate foliaceous stipules are ⅜" to ⅝" long and ¼" to ⅜" wide. The upper surface is Yellow-Green Group 145B and the underside is Yellow-Green Group 145C. The stipules are caducous.

In 1995, the date of initial spring growth was March 29, in Semmes, Ala. After the initial spring flush, there was almost continuous growth until fall, ending October 25, also in Semmes, Ala. When grown in full sun, the internode length of this plant is ⅜" to ⅝". When grown in light shade, the internode length is ½" to ¾". As would be expected, a plant grown in the shade results in a taller, less dense plant with larger leaves.

The average length of terminal growth of the spring flush is about 3 to 4" in full sun and about 4 to 5" when grown in shade. Very little trimming is needed to produce a dense 15" tall and 15" wide three gallon plant during the growing season.

In the landscape, little or no pruning is necessary to produce a dense, low, and spreading shrub in full sun. In shade, however, some trimming may be needed to produce the same effect.

Stems: The young shoots are slender, tomentose, Yellow-Green Group 144A, and when grown in full sun may have a reddish pigmentation (Greyed-Purple Group 185A). The base of the immature petioles may also have this purple color. After one or more years, the stems are generally grey (Greyed-Green Group 197B), glabrous and rugose. The pith is solid and uniform. Young and older stems are densely branched.

Buds: Flower — imbricate, Yellow-Green Group 144A, pubescent, rounded-conical, ½" long, ⅜" wide, borne singularly or in clusters of 2to 3. The 8–10 bracteoles and sepals grade into one another and fall off after the bloom opens. Vegetative — imbricate, Yellow-Green Group 144B, glabrous, angular-conical, ½" long, 3/16" wide, both buds may be present at same node.

Flowers: Perfect, semi-double, closest to Red Group 53B (front and back), glabrous, 2¾" to 3¼" diameter, non-fragrant, axillary, solitary or clusters of 2 to 3, borne on current season's growth; they last on the plant for 5 to 7 days. Pedicels are ⅛" to 3/16" long and Green Group 145A. There are 14–18 true petals which are ¾" to 1¼" long, ¾" to 1⅜" wide, and hemispherical to orbicular in shape. The 8–12 petaloid stamen are ¼" to ⅞" long, ¼" to ⅞" wide, oddly shaped and often inconspicuous. There are 20–30 total petals which have wavy margins and are deciduous after anthesis. The 45 to 50 non-petaloid stamen are fused at ⅓ of the base and ½" to 11/16" long. The filaments are Red Group 52C at the base and Yellow Group 8C distally. The anthers and pollen are Yellow-Orange Group 17A. The pistil is single. The stigma is three parted, Yellow-Green Group 150C, 7/16" to 9/16" long and fused near the ends. Ovaries are pubescent. There is a three to four week flowering period in November to December in Semmes, Ala. In 1995, the first bloom occurred on November 15 and full bloom was on December 2.

Fruit: Loculicidally dehiscent woody capsules are ¾" to 1" long, round or ovate, pubescent, and contain one to three seeds. Fruit remains Yellow-Green Group 144B until ripening to Brown Group 200A in the fall. Mature seed are Brown Group 200D, globose or angular and ½" to ¾" long. During the fall and winter the fruit split open and the seeds fall to the ground. Normally fruit set is not heavy.

Culture: Grows best in partial shade or in full sun as long as the site is not excessively hot. In dense shade, flowering may be suppressed and plants become spindly and open. Prefers a moist, well-drained soil that is rich in organic matter. Responds well to mulching and medium applications of fertilizer; prefers ph 5.0 to 5.5. Very little pruning is needed; adaptable to containers and above ground planters. Excellent for foundation plantings, informal borders, specimen, accent, and sheared or natural low growing hedges. Ideal for coastal regions and warmer parts of Piedmont. Propagated with semi-hardwood cuttings in the fall.

Pests: Scale and spider mites can be a problem.

I claim:

1. A new and unique variety of Camellia plant named 'TDN 1116' as herein shown and described.

* * * * *